US006388067B1

(12) United States Patent
Yu et al.

(10) Patent No.: US 6,388,067 B1
(45) Date of Patent: May 14, 2002

(54) RICE CYSTEINE PROTEINASE GENE PROMOTER

(75) Inventors: Su-May Yu; Wu-Fu Tong, both of Taipei (TW)

(73) Assignee: Academia Sinica, Taipei (TW)

( * ) Notice: Subject to any disclaimer, the term of this patent is extended or adjusted under 35 U.S.C. 154(b) by 0 days.

(21) Appl. No.: 09/480,017

(22) Filed: Jan. 10, 2000

(51) Int. Cl.$^7$ .......................... C07H 21/04; A01H 1/00; A01H 5/00; C12N 15/63; C12N 15/82
(52) U.S. Cl. .................... 536/24.1; 435/320.1; 435/419; 435/468; 800/287; 800/298
(58) Field of Search ............................... 435/320.1, 419, 435/468; 536/24.1; 800/287, 298

(56) References Cited

U.S. PATENT DOCUMENTS 5,689,042 A    11/1997   Amasino et al. ............ 800/205

OTHER PUBLICATIONS

GenBank Accession No. Aq258734, Oct. 1998.*
GenBank Accession No. AB004819, Aug. 1999.*
Shintani et al., "Hormonal Regulation of . . . ," Plant Cell Physiol, 38(11):1242–1248, 1997.
Mikkonen et al., "A major cysteine proteinase . . . ," Plant Molecular Biology, 31:239–254, 1996.
Koehler et al., "Hormonal Regulation, Processing . . . ," The Plant Cell, 2:769–783, 1990.
Kato et al, "Identification and characterization . . . ," Eur. J. Biochem., 239:310–316, 1996.
Ho et al., "Multiple Mode Regulation . . . ," Plant Physiology, 122:1–10, 2000.
Gan et al., "Inhibition of Leaf . . . ," Science, 270:1986–1988, 1995.
Ori et al., "Leaf Senescence Is . . . ," The Plant Cell, 11:1073–1080, 1999.
GenBank Accession No. AF099203, Mar. 17, 1999.

* cited by examiner

*Primary Examiner*—Elizabeth F. McElwain
*Assistant Examiner*—Cynthia Collins
(74) *Attorney, Agent, or Firm*—Fish & Richardson P.C.

(57) ABSTRACT

The invention relates to a rice cysteine proteinase gene promoter, as well as vectors, transformed cells, and transgenic plants containing the promoter.

1 Claim, No Drawings

US 6,388,067 B1

RICE CYSTEINE PROTEINASE GENE PROMOTER

BACKGROUND OF THE INVENTION

Protein degradation is an essential component in plant growth, development, and environmental responses. For example, under nutrient stress condition, such as nitrogen starvation, old proteins are degraded to supply amino acids for new protein synthesis. Protein degradation is also a hallmark of senescence or apoptosis. Cysteine proteinases (CysP) are involved in various protein degradation pathways.

SUMMARY OF THE INVENTION

The invention is based on the discovery of a new promoter derived from a rice CysP gene (designated OsEP3A). The sequence of OsEP3A is shown in FIG. 1. The complete nucleotide sequence of OsEP3A is designated SEQ ID NO:3, while the complete amino acid sequence of the protein encoded by OsEP3A is encoded by SEQ ID NO:4. This sequence begins and ends with an EcoRI site used for cloning as described in the Example below. The upper case nucleotides represent the cDNA sequence, while the lower case nucleotides represent the genomic sequences flanking the cDNA. Nucleotide numberings are relative to the transcription start site. The putative TATA box and polyA signals are underlined. Two putative gibberellic acid (GA3) response elements (GARE) are double underlined. A minimal promoter sequence from −180 to −1 is designated SEQ ID NO:1 (bolded sequence), and the promoter-containing genomic sequence upstream of the transcriptional start site (from −851 to −1) is designated SEQ ID NO:2. A functional signal peptide (in italics) was identified and designated SEQ ID NO:5.

This new promoter was shown to direct expression of a heterologous protein in the aleurone layer of transgenic rice seeds during germination and in cultured rice suspension cells under nitrogen starvation, but not in the presence of nitrogen, a pattern of expression consistent with the metabolic role of the original CysP gene from which the promoter was derived. Consequently, the promoter can be used to regulate and direct expression of a heterologous protein or RNA in transgenic plants or plant cells.

Accordingly, the invention features an isolated nucleic acid including SEQ ID NO:1 (e.g., SEQ ID NO:2), a promoter that hybridizes under stringent conditions to SEQ ID NO:1, or a promoter that is at least 50% (e.g., at least 60, 70, 80, 90, or 95%) identical to SEQ ID NO:1. The nucleic acid of the invention can further included a heterologous sequence to which a promoter containing SEQ ID NO:1 is operably linked, i.e., the promoter directs transcription of the heterologous sequence. The heterologous sequence can encode a protein or polypeptide, e.g., one having the OsEP3A signal peptide (SEQ ID NO:5). The invention also includes vectors and transformed cells harboring a nucleic acid of the invention, as well as transgenic plants (e.g., a transgenic embryo or germinating seed) whose genomic DNA contains a nucleic acid of the invention. The transgenic plant can be a monocot or dicot. The invention further features a method of producing a transgenic plant or organ of a plant (e.g., a seed) by stably introducing a nucleic acid of the invention into a plant cell, and culturing the plant cell under conditions sufficient for the plant cell to form a plant or organ of a plant.

An "isolated nucleic acid" is a nucleic acid which has a non-naturally occurring sequence, or which has the sequence of part or all of a naturally occurring gene but is free of the genes that flank the naturally occurring gene of interest in the genome of the organism in which the gene of interest naturally occurs. The term therefore includes a recombinant DNA incorporated into a vector, into an autonomously replicating plasmid or virus, or into the genomic DNA of a prokaryote or eukaryote. It also includes a separate molecule such as a cDNA, a genomic fragment, a fragment produced by polymerase chain reaction (PCR), or a restriction fragment. It also includes a recombinant nucleotide sequence that is part of a hybrid gene, i.e., a gene encoding a fusion protein. Specifically excluded from this definition are mixtures of DNA molecules, vectors, or clones as they occur in a DNA library such as a cDNA or genomic DNA library. Also excluded are RNA molecules that consist of naturally-occurring sequences (e.g., naturally-occurring mRNA), except where the RNA is in a purified state such that it is at least 90% free of other naturally-occurring RNA species. Thus, a naturally-occurring mRNA in a whole mRNA preparation prepared from a cell would not be an "isolated nucleic acid," but a single mRNA species purified to 90% homogeneity from that whole mRNA preparation would be.

As used herein, "percent identity" of two nucleic acids is determined using the algorithm of Karlin and Altschul (Proc. Natl. Acad. Sci. USA 87:2264–2268, 1990), modified as in Karlin and Altschul (Proc. Natl. Acad. Sci. USA 90:5873–5877, 1993). Such an algorithm is incorporated into the NBLAST and XBLAST programs of Altschul et al. (J. Mol. Biol. 215:403–410, 1990). BLAST nucleotide searches are performed with the NBLAST program, score=100, wordlength=12 to obtain nucleotide sequences homologous to a nucleic acid molecules of the invention. To obtain gapped alignments for comparison purposes, Gapped BLAST is utilized as described in Altschul et al. (Nucleic Acids Res. 25:3389–3402, 1997). When utilizing BLAST and Gapped BLAST programs, the default parameters of the respective programs (e.g., XBLAST and NBLAST) are used. See http://www.ncbi.nlm.nih.gov.

By "hybridizes under stringent conditions" is meant specific and non-covalent equilibrium binding by base-pairing to an immobilized reference nucleic acid in a hybridization solution containing 0.2×SSC (1.75 g/l NaCl, 0.88 g/l Na$_3$citrate.2H$_2$O; pH 7.0) and 0.1% (w/v) sodium dodecylsulfate at 68° C. Washings, if any are required to achieve equilibrium, are carried out with the hybridization solution.

A "heterologous sequence" is a nucleotide sequence that is not naturally operably linked to the OsEP3A promoter in a naturally occurring organism.

A "promoter" is a nucleotide sequence that is capable of directing transcription in at least one context, e.g., when it is operably linked to a heterologous sequence in a plasmid within a plant cell. In other words, a promoter can exist without downstream sequences to transcribe, so long as the promoter sequence can direct transcription when placed upstream of a heterologous sequence in a different context.

The promoter sequence of the invention can be introduced into a variety of plant expression vectors for expressing exogenous proteins in plant cells, transgenic plants, and the aleurone layer of seeds. Such exogenous proteins include anti-ageing or anti-senescent proteins that can prevent tissue damage during stressful conditions, such as during nitrogen starvation. In addition, the isolated nucleic acids of the invention can be used as probes to isolate other promoters and/or genes whose expression is induced under stress or during senescence. For example, nucleotides 18 to 45 (SEQ ID NO:10) or 131 to 170 (SEQ ID NO:11) of SEQ ID NO:1 can be used to screen genomic DNA libraries for genes that are regulated similarly to OsEP3A. Further, the methods of the invention can be used to produce transgenic plants or organs having specialized properties (e.g., longer shelf-life) as a consequence of expressing a heterologous RNA (e.g., a mRNA encoding an anti-ageing protein or an anti-sense RNA that inhibits expression of a senescence-associated gene) in a tissue or organ of a plant.

BRIEF DESCRIPTION OF THE DRAWINGS

FIG. 1 is the sequence of OsEP3A.

Other features or advantages of the present invention will be apparent from the following detailed description, and also from the claims.

DETAILED DESCRIPTION

The invention relates to a new promoter for use in stress-induced regulation of heterologous proteins in plant cells and plants (including embryos, organs, and seeds). Contemplated within the scope of the invention are vectors, transformed cells (produced by genomic integration or extrachromosomal replication of a plasmid), and transgenic plants containing a promoter of the invention operably linked to a heterologous sequence. The heterologous sequence can encode an antisense RNA that blocks the expression of genes during stress.

Vectors, such as expression vectors, can be used to propagate the promoter sequence in bacteria. In this context, it is noted that the promoter sequence can be separated from any heterologous sequence during the propagation step. Vectors can be viral vectors in which the nucleic acids of the invention are ligated into viral genomes. Certain vectors are capable of autonomous replication in a host cell into which they are introduced (e.g., bacterial vectors having a bacterial origin of replication and episomal mammalian vectors). Other vectors are integrated into the genome of a host cell upon introduction into the host cell, and thereby are replicated along with the host genome. Moreover, expression vectors are capable of directing the expression of genes to which they are operatively linked. The invention is intended to include expression vectors and viral vectors (e.g., replication defective retroviruses, adenoviruses, and adeno-associated viruses).

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, particle bombardment, or electroporation.

Genes having a promoter of the invention can be expressed in transgenic plant cells. In order to produce transgenic plants, vectors containing a gene including a promoter of the invention are inserted into the plant genome. Preferably, these recombinant vectors are capable of stable integration into the plant genome. One variable in making a transgenic plant is the choice of a selectable marker gene. A selectable marker gene is used to identify transformed cells against a high background of untransformed cells. Such selectable marker genes include the aminoglycoside phosphotransferase gene of transposon Tn5 (Aph II), which encodes resistance to the antibiotics kanamycin, neomycin, and G418, as well as those genes which encode for resistance or tolerance to glyphosate, hygromycin, methotrexate, phosphinothricin, imidazolinones, sulfonylureas, and triazolophyrimidine herbicides, such as so chlorosulfuron, bromoxynil, dalapon and the like. In addition to a selectable marker gene, it may be desirable to use a reporter gene. In some instances a reporter gene may be used with a selectable marker. Reporter genes allow the detection of a transformed cell and may be used at the discretion of the artisan. These reporter genes are described, e.g., in K. Weising et al., Ann. Rev. Genetics, 22:421, 1988.

Several techniques exist for introducing foreign genes into plant cells, and for obtaining plants that stably maintain and express the introduced gene. Such techniques include acceleration of genetic material on coated particles directly into cells (U.S. Pat. No. 4,945,050). Plant can also be transformed using Agrobacterium technology (U.S. Pat. Nos. 5,177,010, 5,104,310, 5,149,645, 5,469,976, 5,464, 763, 4,940,838, 4,693,976, 5,591,616, 5,231,019, 5,463,174, 4,762,785, 5,004,863, and 5,159,135; and European Patent Applications 116718,290799, 320500, 604662, 627752, 0267159, and 0292435). Other transformation technologies include whiskers technology (see U.S. Pat. Nos. 5,302,523 and 5,464,765). Electroporation technology has also been used to transform plants (see WO 87/06614, WO 92/09696 and WO 93/21335, and U.S. Pat. Nos. 5,472,869 and 5,384, 253). Viral vector expression systems can also be used, such as those described in U.S. Pat. Nos. 5,316,931, 5,589,367, 5,811,653, and 5,866,785.

In addition to numerous technologies for transforming plants, the type of tissue that is contacted with the genes of interest may vary as well. Suitable tissue includes, but is not limited to, embryogenic tissue, callus tissue, hypocotyl, meristem, and the like. Almost all plant tissues may be transformed during dedifferentiation using the appropriate techniques described herein.

Regardless of the transformation system used, a gene containing a promoter of the invention can be incorporated into a gene transfer vector adapted to express the gene in a plant cell by including in the vector an expression control sequence (plant promoter regulatory element) other than a promoter of the invention. The vector can, however, contain various other genes besides the one driven by a promoter of the invention. For these other genes included in the vector, promoter regulatory elements from a variety of sources can be used efficiently in plant cells to express foreign genes. For example, promoter regulatory elements of bacterial origin, such as the octopine synthase promoter, the nopaline synthase promoter, the mannopine synthase promoter may be used. Promoters of viral origin, such as the cauliflower mosaic virus (35S and 19S) are also desirable. Plant promoter regulatory elements also include, but are not limited to, ribulose-1,6-bisphosphate carboxylase small subunit promoter, beta-conglycinin promoter, phascolin promoter, ADH promoter, heat-shock promoters, and tissue specific promoters and the like. Numerous promoters are available to skilled artisans for use at their discretion.

Without further elaboration, it is believed that one skilled in the art can, based on the above disclosure, the isolation of the OsEP3A promoter, and the production transgenic seeds as shown below, utilize the present invention to its fullest extent. The following example is to be construed as merely illustrative of how one skilled in the art can isolate and use the promoters of the invention, and are not limitative of the remainder of the disclosure in any way. Any publications cited in this disclosure are hereby incorporated by reference.

EXAMPLE

To elucidate the hormonal, developmental, and metabolic factors regulating rice CysP gene expression, a rice CysP gene was cloned and characterized as follows.

Plant Material. The rice variety used in this study was *Oryza sativa* L. cv. Tainung 67. Immature seeds were dehulled, sterilized with 2.4% NaOCl for 1 hour, washed extensively with sterile water, and placed on N6D agar medium (Toki, Plant Mol. Biol. Rep. 15:16–21, 1997) for callus induction. After one month, callus derived from scutella was subcultured in fresh N6D medium for transformation, or to a liquid MS medium (Murashige et al., Physiol. Plant 15:473–497, 1962) containing 3% sucrose and 10 nM 2,4-D to establish a suspension cell culture as previously described (Yu et al., J. Biol. Chem. 266:21131–21137, 1991).

Screening of Rice Genomic Library and DNA Sequence, Analysis. Approximately $2 \times 10^6$ recombinant λ phage clones derived from a rice (*Oryza sativa* L. japonica) genomic DNA library (Clontech) were screened. Plaques were lifted on nylon transfer membranes (MSI) and probed with $^{32}$P-labeled random primers produced from a cDNA of EP-B, cloned into pHVEP4 (Kochler et al., Plant Cell 2:769–783, 1990). One positive clone containing a 2.6-kb insert was selected and subcloned into the EcoRI site of pBluescript KS+ (Stratagene), resulting in a plasmid designated pOsEP3A. The complete nucleotide sequence of the rice cysteine proteinase gene OsEP3A was determined from both orientations using a Pharmacia ALF automatic sequencer and a Sequenase Version 2 kit (USB). DNA sequence analysis was performed using the University of Wisconsin GCG software package, version 9.1.

Plasmid Constructions. Plasmid pRY18 carries a 3.8-kb DNA fragment which contains a rice genomic rDNA cluster, including the 3' half portion of the 17S rRNA gene, the complete 5.8 S rRNA gene, and the 5' half portion of the 25S rRNA gene in a pUC13 backbone (Sano et al., Genome 33:209–218, 1990). A 1.1-kb DNA fragment containing the 5' flanking region and the first 28 amino acids of OsEP3A was PCR-amplified using a T7 primer (Stratagene) and the primer 5'-GATATCTGCAGGGTATCGCGGCGCACAG-3' (sequence complementary to positions +195 to +211 of OsEP3A, as shown above; SEQ ID NO:6). This DNA fragment was cleaved with PstI at both ends and cloned into the PstI site of pBX-2 in such a way to allow an in-frame fusion with the gusA coding region (Jefferson et al., Plant Mol. Biol. Rep. 5:387–405, 1987). pBX-2, a pBluescript KSII+ (Stratagene)-derived plasmid, contains the gusA gene and a nopaline synthase gene (Nos) polyadenylation site between the BamHI and XbaI sites. A DNA fragment containing the cauliflower mosaic virus 35S RNA gene (35S) promoter-hygromycin phosphotransferase coding region (Hph)-tumor morphology large gene terminator (Tml 3') was excised from pTRA151 (Zheng et al., Plant Physiol. 97:832–835, 1991) using PstI and EcoRI, and inserted into the same sites in pPZP200 (Hajdukiewicz et al., Plant Mol. Biol. 25:989–994, 1994) to generate pPZP200-H. The virG gene of *Agrobacterium tumefaciens* pTiBo542 (Chen et al., Mol. Gen. Genet. 230:302–309, 1991) was PCR-amplified with blunt ends and inserted into the ScaI site of pPZP200-H to generatepSMY1H. The OsEP3A promoter-gusA-Nos3' chimeric gene was excised from pBX-2 with HindIII and inserted into the HindIII site of pSMY1H to generate pEPGS1.

Printer Extension Analysis. 5'-Primer extension analysis was performed according to Sambrook et al., *Molecular Cloning: A Laboratory Manual*, 2d ed., Cold Spring Harbor Laboratory Press, Cold Spring Harbor, N.Y., 1989. Total RNA was isolated from germinating embryos 3 days after germination. Poly(A)⁺RNA was purified from the total RNA and hybridized with $^{32}$P-labeled primer P2 (5'-ATCGATCGATCGCCACT-3' [SEQ ID NO:7]). The polymerization reaction was performed using SuperScript reverse transcriptase (GIBCO BRL). Dideoxynucleotide sequencing of OsEP3A was performed using the P2 primer to obtain a reference sequence. The extension product and the reference were electrophoresed and visualized by autoradiography.

PCR. DNA PCR of genomic clone pOsEP3A was performed using primers P1 (5'-ATCGCCCTCACCCTCCA-3' [SEQ ID NO:8], positions +1 to +17) and P3 (5'-TGTACGGCGGAGATGGC-3' [SEQ ID NO:9], positions +1240 to +1256). The PCR product, designated P1-3, contained the coding region of OsEP3A and was later used as a probe in genomic DNA Southern blot analysis. Seed mRNA RT-PCR was performed using poly(A)⁺RNA isolated from germinating embryos and P1 and P3, as described in Chan et al., Plant J. 15:685–696, 1998. PCR amplification of pOsEP3A DNA using P1 and P2 generated a 120-bp DNA fragment designated P1-2. P1-2 contains the 5'-untranslated region (5'UTR) of OsEP3A and was later used as a gene-specific probe in genomic DNA Southern blot and RNA Northern blot analyses.

Genomic DNA Southern Blot Analysis. Genomic DNA was isolated from wild type or transformed calli according to Sheu et al., J. Biol. Chem. 271:26998–27004, 1996. Ten milligrams of genomic DNA was digested with restriction enzymes, fractionated in a 0.8% agarose gel, and transferred to a nylon membrane (MSI). Hybridization was performed at 42° C. using $^{32}$P random primer-labelled OsEP3A cDNA (P1-3) or gene-specific DNA (P1-2) as a probe.

Northern Blot Analysis. Total RNA was isolated from various tissues of germinating seeds (Yu et al., Plant Mol. Biol. 30:1277–1289, 1996) and isolated from cultured suspension cells using a TRIZOL reagent (GIBCO BRL). RNA gel blot analysis was performed as described in Thomas, Methods Enzymol. 100:255–266, 1983. Briefly, 10 mg of total RNA was electrophoresed in 1% agarose gel containing 10 mM sodium phosphate buffer (pH 6.5), transferred to a nylon filter, and hybridized with $^{32}$p random primer-labelled P1-2 or rDNA as a probe. The blot was visualized using autoradiography and quantified using a PhosphoImager (Molecular Dynamics).

Transformation. Plasmid pEPGS1 was introduced into *Agrobacterium tumefaciens* strain EHA101 (Hood et al., J. Bacteriol. 168:1291–1301, 1986) using an electroporator (BTX). Calli induced from immature rice seeds were co-cultured with Agrobacterium using the methods described in Hiei et al., Plant J. 6:271–282, 1994; and Toki, supra.

West Blot Analysis. Total proteins were extracted from cultured suspension cells with an extraction buffer (50 mM Tris-HCl [pH 8.8], 1 μM EDTA, 10% glycerol, 1% Triton X-100, 10 mM β-mercaptoethanol, and 0.1% sarkosyl). The culture medium was collected and centrifuged at 18,000×g at 4° C. for 15 minutes to remove cell debris. Western blot analysis was performed as described by Yu et al., 1991, supra. The GUS polyclonal antibodies (Molecular Probes) were diluted 10,000-fold prior to use.

Histochemical Localization Activity. The dehulled seeds with or without embryos were sterilized in 2.4% NaOCl and placed on two pieces of sterile Whatman No. 1 filter paper in a petri dish. A solution containing 1 mM GA$_3$ and 10 mM CaCl$_2$. or sterile water was applied to the filter paper to imbibe the seeds. The seeds were incubated at 28° C. in darkness for various time periods. After incubation, seeds were hand-cut longitudinally in half and stained with 1 mM 5-bromo-4-chloro-3-indolyl b-D-glucuronide (X-gluc) at 37° C. in darkness for 12 hours. The stained seeds were preserved in 70% ethanol and rinsed with water before photography.

To elucidate the hormonal, developmental, and metabolic factors regulating rice CysP gene expression, a rice CysP gene was cloned and characterized using the methods described immediately above. A rice gene that hybridized strongly with the barley CysP cDNA clone pHVEP4 was isolated and designated as OsEP3A. The OsEP3A clone containing 2588 bp was sequenced. The complete coding and the 5'- and 3'-flanking sequences of OsEP3A are shown in the "Summary of the Invention" section above. Comparison with sequence data in GenBank indicated that the coding sequence of OsEP3A matches perfectly with rice pRP60 cDNA which encodes REP-1 (Kato et al., Eur. J. Biochem. 239:310–316, 1996). The intronless feature of OsEP3A is similar to the barley EPB genes (Mikkonen et al., Plant Mol. Biol. 31:239–254, 1996). To verify that OsEP3A is intronless, oligonucleotides P1 and P3 were used as primers for genomic DNA PCR and seed mRNA RT-PCR analyses. A 1.26-kb DNA fragment was amplified from both genomic DNA and mRNA, thereby confirming that OsEP3A is intronless. The transcription start site was mapped to an adenosine 122 bp upstream from the translation initiation codon and designated as +1.

DNA blot analysis was performed to determine the copy number of the CysP gene in the rice genome. By using DNA fragment P1-3 as a probe under very low hybridization stringency, one strong hybridization band and some minor bands were observed irrespective of the restriction enzymes used. This finding indicated that the rice CysP are encoded by a multigene family. By using DNA fragment P1-2 as a probe, only a single band was hybridized. Nucleotide sequence analysis revealed that no significant homology was present among the 5'UTR of OsEP3A and four other rice CysP cDNAs (Watanabe et al., J. Biol. Chem. 266:6897–16902, 1991; and Shintani et al., Plant Cell Physiol. 38:1242–1248, 1997). Based on these results, it is very likely that OsEP3A exists as a single copy gene in the rice genome.

To examine the expression pattern of OsEP3A in germinating seeds, total RNA was purified from embryos and endosperms and subjected to gel blot analysis using P1-2 as a probe. OsEP3A mRNA was barely detectable in the embryos of dry seeds, became detectable 1 hour after imbibition, and then gradually increased with further incubation. Gel blot analysis of RNA in the embryos and endosperms showed that levels of OsEP3A mRNA fluctuated during a 10-day seed germination period. The levels of OsEP3A mRNA in embryos and endosperms reached their first peaks at day 4, declined from day 5 to day 7, then rose again and reached their second peaks at day 8 to day 9 after the onset of seed germination.

Total RNA was also purified from various vegetative tissues of rice at different growth stages and subjected to gel blot analysis using P1-2 as a probe. OsEP3A mRNA was barely detectable in the shoot or root of a 20-day-old seedling, and in the stem and sheath of a 3-month old mature plant. OsEP3A mRNA level was low in the root but high in green leaves and senescing leaves of the mature plant. Quantitation of mRNA indicates that the level of OsEP3A mRNA in the mature green leaves and senescing leaves was 3- and 9-fold, respectively, of that in the mature root. These studies demonstrated that the expression of OsEP3A in vegetative tissues is developmentally and spatially regulated.

To investigate whether the expression of OsEP3A is regulated by environmental nitrogen, rice cells were cultured in MS medium with or without nitrogen sources ($NH_4NO_3$ plus $KNO_3$) for various time periods. Total RNA was purified and subjected to gel blot analysis using P1-2 as a probe. OsEP3A mRNA was not detectable in cells provided with nitrogen, but accumulated in cells starved of nitrogen. Accumulation of OsEP3A mRNA was detected 1 day after nitrogen starvation and increased gradually for up to 12 days. Accumulation of OsEP3A mRNA was suppressed by addition of nitrogen sources into the culture medium and became undetectable within 48 hours after the addition. These results indicated that expression of OsEP3A is suppressed by nitrogen and activated by nitrogen starvation.

To determine whether the expression of OsEP3A was specifically induced by nitrogen starvation and affected by different forms of nitrogen source, rice suspension cells were cultured in medium with or without sucrose or different nitrogen sources. Within an 8-day culture period, the accumulation of OsEP3A mRNA was not or barely detectable in cells cultured in complete MS medium (containing $NH_4NO_3$ plus $KNO_3$) with sucrose, or MS medium without sucrose, but increased significantly in MS medium without any nitrogen source. The accumulation of OsEP3A mRNA was also not detectable in MS medium with either $NH_4NO_3$ or $KNO_3$ as the nitrogen source. These results demonstrated that expression of OsEP3A is specifically induced by nitrogen starvation and not by sucrose starvation. OsEP3A mRNA in the nitrogen-starved cells could be significantly repressed by the addition of asparagine, glutamine, glutamate, $NH_4Cl$, or $NH_4NO_3$ into the MS medium as a nitrogen source. Also, addition of $KNO_3$ into the MS medium as a nitrogen source partially suppressed the accumulation of OsEP3A mRNA. This result further demonstrated that a metabolizable nitrogen source can suppress the expression of OsEP3A.

To investigate the role of the promoter in the regulation of OsEP3A expression in rice, a 1.1-kb DNA fragment containing the OsEP3A promoter and sequence encoding the signal peptide (SEQ ID NO:5) was fused in-frame at the 5' end of the gusA gene as described above to subsequently produce pEPGS. This plasmid was introduced into Agrobacterium for rice transformation. Thirty transgenic lines were regenerated and four lines containing a single copy of the gusA gene were selected for further study. Callus derived from scutella of transgenic seeds was cultured as suspension cells. The transformed suspension cells were then cultured in medium with or without nitrogen. Total RNA was purified and subjected to gel blot analysis using the gusA cDNA and P1-2 as probes. Accumulation of both gusA and OsEP3A mRNAs was detected in coils starved of nitrogen but not in cells provided with nitrogen. No gusA mRNA was detected in non-transformed cells. The levels of OsEP3A mRNA in the four transgenic lines were fairly similar while the levels of gusA mRNA varied from line to line, indicating a position effect on transgene expression.

Cultured suspension cells of transgenic line 14 were selected for further study of the function of the putative signal peptide sequence in protein secretion. Cells were grown in medium with or without nitrogen for 10 days and proteins were extracted from cells or collected from the culture medium and subjected to Western blot analysis using GUS antibodies. GUS was detected in cells and medium only when cells were starved of nitrogen. This result indicated that the OsEP3A signal peptide (SEQ ID NO:5) was capable of directing translocation of GUS through the secretory pathway of transformed cells and into the culture medium.

To investigate the role of the OsEP3A promoter in the temporal, spatial and hormonal regulation of OsEP3A expression during rice seed germination, histochemical GUS assays of transgenic seeds carrying the OsEP3A-gusA chimeric gene were performed. In longitudinally cut germinating seeds, GUS activity was detected in the scutellar epithelium within 1 day after germination. This activity spread into the adjacent aleurone layer by day 3 and finally covered the entire aleurone layer by day 5. In cross-cut germinating seeds, GUS activity was not detected in the nontransformed aleurone layer by day 3, but was first detected in the ventral side of the aleurone layer within 1 day after germination. GUS activity then spread into the dorsal side of the aleurone layer by day 3, and finally almost the entire aleurone layer by day 5.

To examine the effect of $GA_3$ on the expression of the OsEP3A-gusA gene in seeds, de-embryonated transgenic rice seeds were treated with $GA_3$ for various time periods. In $GA_3$-treated, longitudinally cut seeds, GUS activity was not detected in the nontransformed de-embryonated seed by day 3, but was first detected in the ventral side of the aleurone layer within 1 day, then in both the ventral and dorsal sides of the aleurone layer by day 3, and finally in the entire aleurone layer by day 5. These results indicated that a transgene whose expression is directed by the OsEP3A promoter is regulated spatially and temporally.

What is claimed is:

1. An isolated nucleic acid comprising SEQ ID NO:2.

\* \* \* \* \*

SEQUENCE LISTING

<160> NUMBER OF SEQ ID NOS: 11

<210> SEQ ID NO 1
<211> LENGTH: 180
<212> TYPE: DNA
<213> ORGANISM: Oryza sativa

<400> SEQUENCE: 1

```
atcttcgacg ccattggcaa ctcacgtagc ccgccgctaa cgtagcagcc g tccatccca      60 actccctagc tgaatctgac accatcgcac gcatctttct gttaccccca t ttaaatccg     120 tctcgtttcc cgccgcaaat cccagctata aatacgtctc ctcccttctc c ttcctcctc     180
```

<210> SEQ ID NO 2
<211> LENGTH: 851
<212> TYPE: DNA
<213> ORGANISM: Oryza sativa

<400> SEQUENCE: 2

```
gaattcccgt gggtagcggt gcgtgaaatt ggagcagcct gaagccctga a ccgtgaaaa      60 actgggctgt gagactcaga gcgcgaacca aatctgtcat ggagaagata c tccctccgt     120 actcgtaaag aaaatcgttt agaacaatgt ttaagtcaaa ccttgagaat a taaatcatg     180 aataactatc aagttgttga gttttaaaat ataaaaatta tatgaataga t ttgtcttga     240 aaaataacat acatatatca cttttttaatg aatatttta taaaaataag a agttaaagt     300 tgtgttttag agaccgtgtc gctgtcctaa ataagttact ttacgagtat g gagggagta     360 atgagctagc cgatcaaccg acgtatcaac aacgcggtgg tctctgcggc t ctgctcatc     420 gcaaccaatt cctacacgcc gcgcaggcag ccctcggcct ccacgaccgc c attaatacc     480 gtcctagcca agctacgatc aatcacagag caaagcagcc attcctcacg t cacgtagcc     540 cgaccaccca gtgataaact tcccagcaac ccagtactag catccataaa a ttgcacacc     600 taagctagct acactagatt caatcaagtc atgaacaaaa accgatcgat c cgtatttga     660 atctggccag aatcttcgac gccattggca actcacgtag cccgccgcta a cgtagcagc     720 cgtccatccc aactccctag ctgaatctga caccatcgca cgcatctttc t gttaccccc     780 atttaaatcc gtctcgtttc ccgccgcaaa tcccagctat aaatacgtct c ctcccttct     840 ccttcctcct c                                                          851
```

<210> SEQ ID NO 3
<211> LENGTH: 2588
<212> TYPE: DNA
<213> ORGANISM: Oryza sativa
<220> FEATURE:

<221> NAME/KEY: CDS
<222> LOCATION: (974)...(2077)

<400> SEQUENCE: 3

```
gaattcccgt gggtagcggt gcgtgaaatt ggagcagcct gaagccctga a ccgtgaaaa      60 actgggctgt gagactcaga gcgcgaacca aatctgtcat ggagaagata c tccctccgt     120 actcgtaaag aaaatcgttt agaacaatgt ttaagtcaaa ccttgagaat a taaatcatg     180 aataactatc aagttgttga gttttaaaat ataaaaatta tatgaataga t ttgtcttga     240 aaaataacat acatatatca cttttttaatg aatattttta taaaaataag a agttaaagt    300 tgtgttttag agaccgtgtc gctgtcctaa ataagttact ttacgagtat g gagggagta    360 atgagctagc cgatcaaccg acgtatcaac aacgcggtgg tctctgcggc t ctgctcatc    420 gcaaccaatt cctacacgcc gcgcaggcag ccctcggcct ccacgaccgc c attaatacc    480 gtcctagcca agctacgatc aatcacagag caaagcagcc attcctcacg t cacgtagcc    540 cgaccaccca gtgataaact tcccagcaac ccagtactag catccataaa a ttgcacacc    600 taagctagct acactagatt caatcaagtc atgaacaaaa accgatcgat c cgtatttga    660 atctggccag aatcttcgac gccattggca actcacgtag cccgccgcta a cgtagcagc    720 cgtccatccc aactccctag ctgaatctga caccatcgca cgcatctttc t gttacccc    780 atttaaatcc gtctcgtttc ccgccgcaaa tcccagctat aaatacgtct c ctcccttct    840 ccttcctcct catcgccctc accctccaat tccaatccct cccaagaact a gctgatcac    900 gacgagcagc tagtccactg ctactgcgat cgatcggttg caaagttaat t aattagtgg    960 cgatcgatcg atc atg ggg agg gtt att agc agc t gg agg gtt ctt gcg     1009
            Met Gly Arg Val Ile Ser Ser Trp Arg Val Leu Ala
              1               5                  10 gtg gtg gct gct ttg atg gcc atg gcg gcg g tg gag ctg tgc gcc gcg    1057
Val Val Ala Ala Leu Met Ala Met Ala Ala  Val Glu Leu Cys Ala Ala
         15                  20                  25 ata ccg ttc gac gag agg gat ttg gag tcc g ac gag gcg ctg tgg gat    1105
Ile Pro Phe Asp Glu Arg Asp Leu Glu Ser A sp Glu Ala Leu Trp Asp
     30                  35                  40 ctg tac gag cgg tgg cag gag cac cac cac g tg ccg cgc cac cac ggc    1153
Leu Tyr Glu Arg Trp Gln Glu His His His V al Pro Arg His His Gly
 45                  50                  55                  60 gag aag cac cgc cgg ttc ggc gcg ttc aag g ac aac gtg agg tac atc    1201
Glu Lys His Arg Arg Phe Gly Ala Phe Lys A sp Asn Val Arg Tyr Ile
                 65                  70                  75 cac gag cac aac aag cgc gcg ccg ggc tac c ct ccg ctc aac cgc ttc    1249
His Glu His Asn Lys Arg Ala Pro Gly Tyr P ro Pro Leu Asn Arg Phe
             80                  85                  90 ggc gac atg ggc aga gag gag ttc cgc gcc a cg ttc gcc ggg tcc cac    1297
Gly Asp Met Gly Arg Glu Glu Phe Arg Ala T hr Phe Ala Gly Ser His
         95                 100                 105 gcc aac gac ctc cgc cgc gac ggc ctc gcc g cg ccg ccg ctc ccg ggg    1345
Ala Asn Asp Leu Arg Arg Asp Gly Leu Ala A la Pro Pro Leu Pro Gly
     110                 115                 120 ttc atc tac gag ggc gtc cgc gac ctc ccc c gc gcc gtc gac tgg cgc    1393
Phe Ile Tyr Glu Gly Val Arg Asp Leu Pro A rg Ala Val Asp Trp Arg
125                 130                 135                 140 cgc aag ggc gcg gtc acc ggc gtc aag gac c ag ggc aag tcc ggc agc    1441
Arg Lys Gly Ala Val Thr Gly Val Lys Asp G ln Gly Lys Ser Gly Ser
                145                 150                 155 tgc tgg gcg ttc tcc acg gtg gtg tcc gtg g ag ggc atc aac gcg atc    1489
Cys Trp Ala Phe Ser Thr Val Val Ser Val G lu Gly Ile Asn Ala Ile
```

-continued

| | |
|---|---|
| cgg acg ggg cgg ctg gtg tcg ctg tcg gag c ag gag ctg atc gac tgc<br>Arg Thr Gly Arg Leu Val Ser Leu Ser Glu G ln Glu Leu Ile Asp Cys<br>    175                      180                      185 | 1537 |
| gac acg gcg gac aac agc ggc tgc cag ggc g gg ctc atg gag aac gcg<br>Asp Thr Ala Asp Asn Ser Gly Cys Gln Gly G ly Leu Met Glu Asn Ala<br>    190                      195                      200 | 1585 |
| ttc gag tac atc aag cac agc ggc ggc atc a cc acc gag tcc gcc tac<br>Phe Glu Tyr Ile Lys His Ser Gly Gly Ile T hr Thr Glu Ser Ala Tyr<br>205                      210                      215                  220 | 1633 |
| ccg tac cgc gcc gcc aac gga acg tgc gac g cc gtc cgc gcg cgc ggc<br>Pro Tyr Arg Ala Ala Asn Gly Thr Cys Asp A la Val Arg Ala Arg Gly<br>                      225                      230                      235 | 1681 |
| ggg ctg gtg gtg atc gac ggg cac cag aac g tg ccg gcc aac agc gag<br>Gly Leu Val Val Ile Asp Gly His Gln Asn V al Pro Ala Asn Ser Glu<br>    240                      245                      250 | 1729 |
| gcc gcg ctc gcc aag gcc gtc gcc aac cag c cc gtc tcc gtc gcc atc<br>Ala Ala Leu Ala Lys Ala Val Ala Asn Gln P ro Val Ser Val Ala Ile<br>                      255                      260                      265 | 1777 |
| gac gcc ggc gac cag tcc ttc cag ttc tac t cc gac ggc gtc ttc gcc<br>Asp Ala Gly Asp Gln Ser Phe Gln Phe Tyr S er Asp Gly Val Phe Ala<br>    270                      275                      280 | 1825 |
| ggc gac tgc ggc acc gac ctc gac cac ggc g tc gcg gtg gtc ggc tac<br>Gly Asp Cys Gly Thr Asp Leu Asp His Gly V al Ala Val Val Gly Tyr<br>285                      290                      295                  300 | 1873 |
| ggc gag acc aac gac ggc acg gag tac tgg a tc gtc aag aac tcg tgg<br>Gly Glu Thr Asn Asp Gly Thr Glu Tyr Trp I le Val Lys Asn Ser Trp<br>                      305                      310                      315 | 1921 |
| ggc aca gcc tgg ggc gag ggc ggc tac atc c gg atg cag cgc gac tcc<br>Gly Thr Ala Trp Gly Glu Gly Gly Tyr Ile A rg Met Gln Arg Asp Ser<br>    320                      325                      330 | 1969 |
| ggc tac gac ggc ggc ctc tgc ggc atc gcc a tg gaa gcc tcc tac ccc<br>Gly Tyr Asp Gly Gly Leu Cys Gly Ile Ala M et Glu Ala Ser Tyr Pro<br>                      335                      340                      345 | 2017 |
| gtc aag ttc tcg cca aat cgt gtc acg cca a gg cgc gcc ctt ggg cca<br>Val Lys Phe Ser Pro Asn Arg Val Thr Pro A rg Arg Ala Leu Gly Pro<br>    350                      355                      360 | 2065 |
| aag gaa acc cag tgatcgagcc ggcgccatct ccgccgtaca c gtgcccgcc<br>Lys Glu Thr Gln<br>365 | 2117 |
| tacgagcctg gatcaacggc tctggtcgcg tctcctcctc cagcttgcaa a atggtgcta | 2177 |
| ttattgttgc tgctctttgt taattgcctt gtgtttatgt aattcgtgtg a ggcgatcag | 2237 |
| ggaaaagaat tacctgaaat cgtctaagtt actagtgtta tttcgtgtgt g ctaaataag | 2297 |
| ttttagatgt gaggtgaggt cgatctatca tgtaatgtac tgaacttata t gtggtgttc | 2357 |
| ttcgtggcac cgggaaatat atataagaag gttgttgtta tgactaaggt t atgccaaat | 2417 |
| ttcatccaaa aaagactaag gttatgccaa atttcatcca aaaaaagtt a tctcaattg | 2477 |
| cttcagtttt tagcttgtct cgctgggcgt tcctatgact tatgtgagtt a cgactcgtg | 2537 |
| ggattcgcaa ccaaaatcga agacgagagc tttgcaaccg gagaggaatt c | 2588 |

<210> SEQ ID NO 4
<211> LENGTH: 368
<212> TYPE: PRT
<213> ORGANISM: Oryza sativa

<400> SEQUENCE: 4

Met Gly Arg Val Ile Ser Ser Trp Arg Val L eu Ala Val Val Ala Ala

-continued

```
                1               5                    10                   15
          Leu Met Ala Met Ala Ala Val Glu Leu Cys A la Ala Ile Pro Phe Asp
                         20                  25                  30
          Glu Arg Asp Leu Glu Ser Asp Glu Ala Leu T rp Asp Leu Tyr Glu Arg
                         35                  40                  45
          Trp Gln Glu His His Val Pro Arg His H is Gly Glu Lys His Arg
                 50                      55                  60
          Arg Phe Gly Ala Phe Lys Asp Asn Val Arg T yr Ile His Glu His Asn
           65                      70                  75                  80
          Lys Arg Ala Pro Gly Tyr Pro Leu Asn A rg Phe Gly Asp Met Gly
                             85                  90                  95
          Arg Glu Glu Phe Arg Ala Thr Phe Ala Gly S er His Ala Asn Asp Leu
                         100                 105                 110
          Arg Arg Asp Gly Leu Ala Ala Pro Pro Leu P ro Gly Phe Ile Tyr Glu
                         115                 120                     125
          Gly Val Arg Asp Leu Pro Arg Ala Val Asp T rp Arg Arg Lys Gly Ala
                         130                 135                 140
          Val Thr Gly Val Lys Asp Gln Gly Lys Ser G ly Ser Cys Trp Ala Phe
           145                 150                 155                 160
          Ser Thr Val Val Ser Val Glu Gly Ile Asn A la Ile Arg Thr Gly Arg
                             165                 170                 175
          Leu Val Ser Leu Ser Glu Gln Glu Leu Ile A sp Cys Asp Thr Ala Asp
                         180                 185                 190
          Asn Ser Gly Cys Gln Gly Gly Leu Met Glu A sn Ala Phe Glu Tyr Ile
                         195                 200                 205
          Lys His Ser Gly Gly Ile Thr Thr Glu Ser A la Tyr Pro Tyr Arg Ala
                 210                 215                     220
          Ala Asn Gly Thr Cys Asp Ala Val Arg Ala A rg Gly Gly Leu Val Val
           225                 230                 235                 240
          Ile Asp Gly His Gln Asn Val Pro Ala Asn S er Glu Ala Ala Leu Ala
                         245                 250                 255
          Lys Ala Val Ala Asn Gln Pro Val Ser Val A la Ile Asp Ala Gly Asp
                         260                 265                 270
          Gln Ser Phe Gln Phe Tyr Ser Asp Gly Val P he Ala Gly Asp Cys Gly
                         275                 280                 285
          Thr Asp Leu Asp His Gly Val Ala Val Val G ly Tyr Gly Glu Thr Asn
                 290                 295                     300
          Asp Gly Thr Glu Tyr Trp Ile Val Lys Asn S er Trp Gly Thr Ala Trp
           305                 310                 315                 320
          Gly Glu Gly Gly Tyr Ile Arg Met Gln Arg A sp Ser Gly Tyr Asp Gly
                             325                 330                 335
          Gly Leu Cys Gly Ile Ala Met Glu Ala Ser T yr Pro Val Lys Phe Ser
                         340                 345                 350
          Pro Asn Arg Val Thr Pro Arg Arg Ala Leu G ly Pro Lys Glu Thr Gln
                         355                 360                 365

<210> SEQ ID NO 5
<211> LENGTH: 22
<212> TYPE: PRT
<213> ORGANISM: Oryza sativa

<400> SEQUENCE: 5

Met Gly Arg Val Ile Ser Ser Trp Arg Val L eu Ala Val Val Ala Ala
           1               5                    10                   15
```

```
Leu Met Ala Met Ala Ala
         20

<210> SEQ ID NO 6
<211> LENGTH: 28
<212> TYPE: DNA
<213> ORGANISM: Artificial Sequence
<220> FEATURE:
<223> OTHER INFORMATION: synthesized primer

<400> SEQUENCE: 6
gatatctgca gggtatcgcg gcgcacag                                28

<210> SEQ ID NO 7
<211> LENGTH: 17
<212> TYPE: DNA
<213> ORGANISM: Artificial Sequence
<220> FEATURE:
<223> OTHER INFORMATION: synthesized primer

<400> SEQUENCE: 7
atcgatcgat cgccact                                           17

<210> SEQ ID NO 8
<211> LENGTH: 17
<212> TYPE: DNA
<213> ORGANISM: Artificial Sequence
<220> FEATURE:
<223> OTHER INFORMATION: synthesized primer

<400> SEQUENCE: 8
atcgccctca ccctcca                                           17

<210> SEQ ID NO 9
<211> LENGTH: 17
<212> TYPE: DNA
<213> ORGANISM: Artificial Sequence
<220> FEATURE:
<223> OTHER INFORMATION: synthesized primer

<400> SEQUENCE: 9
tgtacggcgg agatggc                                           17

<210> SEQ ID NO 10
<211> LENGTH: 28
<212> TYPE: DNA
<213> ORGANISM: Oryza sativa

<400> SEQUENCE: 10
caactcacgt agcccgccgc taacgtag                               28

<210> SEQ ID NO 11
<211> LENGTH: 40
<212> TYPE: DNA
<213> ORGANISM: Oryza sativa

<400> SEQUENCE: 11
cgccgcaaat cccagctata aatacgtctc ctcccttctc                  40
```